US007135498B1

(12) United States Patent
Chopp et al.

(10) Patent No.: US 7,135,498 B1
(45) Date of Patent: *Nov. 14, 2006

(54) NITRIC OXIDE DONORS FOR INDUCING NEUROGENESIS

(75) Inventors: Michael Chopp, Southfield, MI (US); Rui Lan Zhang, Troy, MI (US)

(73) Assignee: Henry Ford Health System, Detroit, MI (US)

( * ) Notice: Subject to any disclaimer, the term of this patent is extended or adjusted under 35 U.S.C. 154(b) by 129 days.

This patent is subject to a terminal disclaimer.

(21) Appl. No.: 10/018,201

(22) PCT Filed: Jun. 14, 2000

(86) PCT No.: PCT/US00/16353

§ 371 (c)(1),
(2), (4) Date: Apr. 2, 2002

(87) PCT Pub. No.: WO00/76318

PCT Pub. Date: Dec. 21, 2000

Related U.S. Application Data

(60) Provisional application No. 60/138,971, filed on Jun. 14, 1999.

(51) Int. Cl.
*A01N 37/12* (2006.01)
(52) U.S. Cl. ............... 514/565; 514/482; 514/611; 424/422
(58) Field of Classification Search ............... 514/45
See application file for complete search history.

(56) References Cited

U.S. PATENT DOCUMENTS

| | | | |
|---|---|---|---|
| 4,439,196 A | 3/1984 | Higuchi | |
| 4,447,224 A | 5/1984 | DeCant, Jr. et al. | |
| 4,447,233 A | 5/1984 | Mayfield | |
| 4,475,196 A | 10/1984 | La Zor | |
| 4,486,194 A | 12/1984 | Ferrara | |
| 4,487,603 A | 12/1984 | Harris | |
| 4,666,828 A | 5/1987 | Gusella | |
| 4,683,202 A | 7/1987 | Mullis | |
| 4,801,531 A | 1/1989 | Frossard | |
| 4,925,678 A | 5/1990 | Ranney | |
| 4,959,217 A | 9/1990 | Sanders et al. | |
| 5,167,616 A | 12/1992 | Haak et al. | |
| 5,169,383 A | 12/1992 | Gyory et al. | |
| 5,192,659 A | 3/1993 | Simons | |
| 5,225,182 A | 7/1993 | Sharma | |
| 5,272,057 A | 12/1993 | Smulson et al. | |
| 5,385,940 A * | 1/1995 | Moskowitz | 514/565 |
| 6,284,763 B1 * | 9/2001 | Adams et al. | 514/248 |

FOREIGN PATENT DOCUMENTS

| | | | |
|---|---|---|---|
| WO | WO 95 12394 | 5/1995 | |
| WO | WO 99 37616 | 7/1999 | |
| WO | WO 00/76318 A | 12/2000 | |

OTHER PUBLICATIONS

Bredt and Snyder, Annual Review of Biochemistry, vol. 63:175-195 (1994).*
Poluha, Wojciech et al., Journal of Biological Science vol. 272:38 24002-24007 (1997).*
Schipp R. and Gebauer M. invert Neurosci vol. 4:9-15 (1999).*
Shaun Hindley, Bernard H. J. Juurlink, John W. Gysbers Pamela J. Maddlemis, Mary A. R. Herman and Micheal P. Rathbone. Journal of Neuroscience Research vol. 47:r427-439 (1997).*
Vance G. Nielsen, Manuel S. Baird, Lan Chen, and Sadis Matalon Am. J. of Crit. Care Med. vol. 1611154-1160 (2000).*
Ausubel et al., *Current Protocols in Molecular Biology*, John Wiley and Sons, Baltimore, Maryland (1989).
Burke and Olson, Methods in Enzymology, vol. 194, "Preparation of Clone Libraries in Yeast Artificial-Chromosome Vectors", eds. C. Guthrie and G. Fink, Academic Press, Inc., Chap. 17, pp. 251-270, 1991.
Capecchi, MR. "Altering the genome by homologous recombination", Science 244:1288-1292, 1989.
Davies, NP., Rosewell, IR., Brüggemann, M. "Targeted alterations in yeast artificial chromosomes for interspecies gene transfer", Nucleic Acids Research, vol. 20, No. 11, pp. 2693-2698, 1992.
Dickinson, P., Kimber, WL., Kilanowski, FM., Stevenson, B.J., Porteous, DJ., Dorin, JR. "High frequency gene targeting using insertional vector", Human Molecular Genetics, vol. 2, No. 8, pp. 1299-1302, 1993.
Duff and Lincoln. "Insertion of a pathogenic mutation into a yeast artificial chromosome containing the human APP gene and expression in ES cells", Research Advances in Alzheimer's Disease and Related Disorders, 1995.
Huxley, C., Hagino, Y., Schlessinger, D., Olson, MV. "The human HPRT gene on a yeast artificial chromosome is functional when transferred to mouse cells by cell fusion", Genomics, 9:742-750 1991.
Innis MA, Gelfan DH, Sninsky, JJ, White TJ (eds.) "PCR Protocols: A Guide to Methods and Applications," Academic Press, San Diego, CA 1990.

(Continued)

*Primary Examiner*—Christopher S. F. Low
*Assistant Examiner*—Shirley V. Gembeh
(74) *Attorney, Agent, or Firm*—Kohn & Associates, PLLC; Kenneth I. Kohn

(57) ABSTRACT

There is provided a method of promoting neurogenesis by administering a therapeutic amount of a nitric oxide donor compound to a patient in need of neurogenesis promotion. Also provided is a compound for providing neurogenesis having an effective amount of a nitric oxide donor sufficient to promote neurogenesis. A nitric oxide compound for promoting neurogenesis is also provided. Further, a method of augmenting the production of brain cells and facilitating cellular structural and receptor changes by administering an effective amount of a nitric oxide donor compound to a site in need of augmentation is provided. There is provided method of increasing both neurological and cognitive function by administering an effective amount of a nitric oxide donor compound to a patient.

3 Claims, 11 Drawing Sheets

OTHER PUBLICATIONS

Jakobovis, A., Moore, AL., Green, LL., Vergara, GJ., Maynard-Currie, CE., Austin, HA., Klapholz, S. "Germ-line transmission and expression of a human-derived yeast artificial chromosome", Nature, vol. 362, pp. 255-261, 1993.

Johnson, S., Bird, RE. "Construction of single-chain Fvb derivations of monoclonal antibodies and their production of *Escherichia coli*", Methods in Enzymology (JJ Langone, ed.; Academic Press New York, NY) 203:88-99, 1991.

Lamb et al. "Introduction and expression of the 400 kilobase *precursor amyloid protein* gene in transgenic mice", Nature Genetics, vol. 5, pp. 22-29, 1993.

Mernaugh and Mernaugh. "An overview of phage-displayed recombinant antibodies", Molecular Methods in Plant Pathology (RP Singh and US Singh, eds.; CRC Press Inc., Boca Raton, FL) pp. 359-365, 1995.

Mishell, BB., Shiigi, SM. Selected Methods in Cellular Immunology, W.H. Freeman and Company, New York, 1981.

Sambrook et al., *Molecular Cloning: A Laboratory Manual*, Cold Spring Harbor Laboratory Press, New York (1989).

Testoni N. Martinelli G, Farabegoli P. Zaccaria A, Amabile M, Raspadori D, Pelliconi S, Zuffa E, Carboni C, Tura S. "A New Method of "In-Cell Reverse Transcriptase-Polymerase Chain Reaction" for the Detection of BCR/ABL Transcript in Chronic Myeloid Leukemia Patients," Blood, vol. 87, No. 9, 3822-3827, May 1, 1996.

Van Wagenen Stefanie, et al., Regulation of neuronal growth cone filopodia by nitric oxide, Journal of Neurobiology, vol. 39, No. 2, May 1999, pp. 168-185.

* cited by examiner

NITRIC OXIDE DONORS FOR INDUCING NEUROGENESIS

CROSS REFERENCE TO RELATED APPLICATIONS

The present application is a National Phase Concerning a Filing Under 35 U.S.C. 371, claiming the benefit of priority of PCT/US00/16353, filed Jun. 14, 2000, which claims the benefit of priority of U.S. Provisional Ser. No. 60/138,971, filed Jun. 14, 1999, both of which are incorporated herein by reference.

BACKGROUND OF THE INVENTION

1. Technical Field

The present application relates to a method and compound for promoting neurogenesis and promoting recovery after neural injury and neurodegeneration. More specifically, the present invention relates to a method and composition for promoting neurogenesis and plasticity in the nervous system.

2. Background of the Invention

Stroke occurs when a section of the brain becomes infarcted, resulting in death of brain tissue from interruption of cerebral blood supply. Cerebral infarcts associated with acute stroke cause sudden and dramatic neurological impairment. Stroke is the third most common cause of death in the adult population of the United States, and is a major cause of disability.

Pharmacological interventions have attempted to maximize the blood flow to stroke affected brain areas which might be able to survive, but clinical effectiveness has proven elusive. As stated in Harrison's Principles of Internal Medicine ($9^{th}$ Ed., 1980, p. 1926), "despite experimental evidence that . . . [cerebral vasodilators] increase the cerebral blood flow, as measured by the nitrous oxide method, they have not proved beneficial in careful studies in human stroke cases at the stage of transient ischemic attacks, thrombosis-in-evolution, or in the established stroke. This is true of nicotinic acid, Priscoline, alcohol, papaverine, and inhalation of 5% carbon dioxide . . . In opposition to the use of these methods is the suggestion that vasodilators are harmful rather than beneficial, since by lowering the systemic blood pressure they reduce the intracranial anastomotic flow, or by dilating blood vessels in the normal parts of the brain they steal blood from the infarct."

It would therefore be useful to develop a compound and method for lessening the effects of stroke by enabling neurogenesis to occur.

SUMMARY OF THE INVENTION

According to the present invention, there is provided a method of promoting neurogenesis by administering a therapeutic amount of a nitric oxide donor to a patient in need of neurogenesis promotion. Neurogenesis is also promoted in non injured brain. Also provided is a compound for inducing neurogenesis including an effective amount of a nitric oxide donor sufficient to promote neurogenesis. A nitric oxide compound for promoting neurogenesis is also provided. Further, a method of augmenting the production of neurons by administering an effective amount of a nitric oxide donor compound to a site in need of augmentation is provided. There is provided a method of increasing both neurological and cognitive function by administering an effective amount of a nitric oxide donor compound to a patient.

BRIEF DESCRIPTION OF THE DRAWINGS

Other advantages of the present invention will be readily appreciated as the same becomes better understood by reference to the following detailed description when considered in connection with the accompanying drawings wherein.

DETAILED DESCRIPTION

Figure 1:
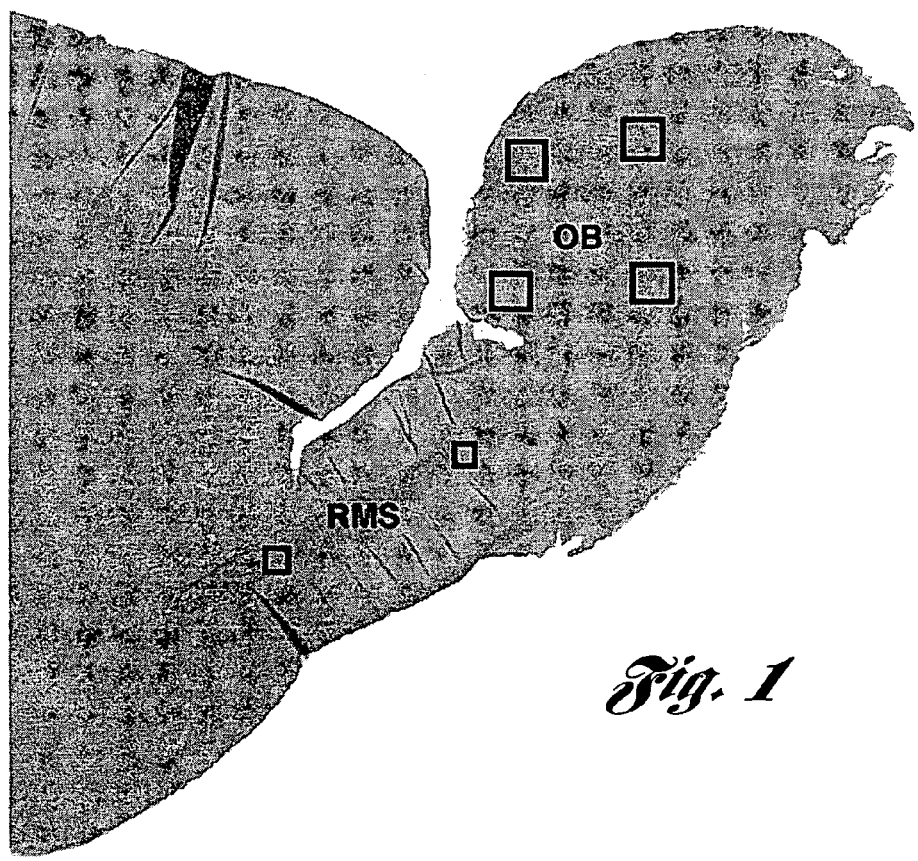
FIG. 1 is a photograph showing the BrdU-positive nuclei in the selected areas.

Generally, the present invention provides a method and compound for promoting neurogenesis. More specifically, the present invention provides a method and compound for promoting neurogenesis utilizing an effective amount of a nitric oxide donor which promotes the neurogenesis. The neurogenesis can be required in various locations, including but not limited to, the brain, CNS, ear or any other location containing damaged neurons therein.

By "nitric oxide donor" it is meant a compound which is able to donate nitric oxide or promote increase of nitric oxide. There are families of compounds which donate nitric oxide. Included among these compounds are: DETANONOate (DETANONO, NONOate or 1-substituted diazen-1-ium-1,2-diolates are compounds containing the [N(O)NO]-functional group: DEA/NO; SPER/NO: DETA/NO; OXI/NO; SULFI/NO; PAPA/NO; MAHMA/NO and DPTA/NO), PAPANONOate, SNAP (S-nitroso-N-acetylpenicillamine), sodium nitroprusside, and sodium nitroglycerine. There are compounds which promote the increase in nitric oxide, such as phosphodiesterase inhibitors and L-arginine.

By "promoting neurogenesis" as used herein, it is meant that neural growth is promoted or enhanced. This can include, but is not limited to, new neuronal growth or enhanced growth of existing neurons, as well as growth and proliferation of parenchymal cells and cells that promote tissue plasticity. Neurogenesis also encompasses, but is not limited to, neurite and dendritic extension and synaptogenesis.

By "augmentation" as used herein, it is meant that growth is either enhanced or suppressed as required in the specific situation. Therefore, if additional neuron growth is required, the addition of a nitric oxide donor increases this growth. Nitric oxide donors, or sources of nitric oxide, prime cerebral tissue to compensate for damage brought on by injury, neurodegeneration, or aging by enhancing receptor activation and promoting cellular morphological change and cellular proliferation.

By "neurological" or "cognitive" function as used herein, it is meant that the neural growth in the brain enhances the patient's ability to think, function, or more. Humans treated with nitric oxide have increased production of brain cells that facilitate improved cognition, memory and motor function. Further, patients suffering from neurological disease or injury when treated with nitric oxide have improved cognition, memory, and motor function.

The purpose of the present invention is to promote an improved outcome from ischemic cerebral injury, or other neuronal injury, by inducing neurogenesis and cellular changes that promote functional improvement. Patients suffer neurological and functional deficits after stroke, CNS injury and neurodegenerative disease. These findings provide a means to enhance brain compensatory mechanism to improve function after CNS damage or degeneration. The induction of neurons and cellular changes induced by nitric oxide administration will promote functional improvement after stroke, injury, aging and degenerative disease. This approach can also provide benefit to patients suffering from other neurological disease such as, but not limited to, ALS, MS, and Huntingtons Nitric oxide administered at propitious times after CNS injury promotes neurogenesis in brain and is able to facilitate neurogenesis. The primary mechanism for such production is that NO activates glutamate receptors. These glutamate receptors promote long term potentiation and subsequently induce regeneration of neurons. As an initial experiment, DETA/NO was employed, a compound with a long half-life (~50 hours) which produces NO. Increased numbers of new neurons were identified when this compound was administered at and beyond 24 hours after onset of stroke.

The experimental data included herein show that a pharmacological intervention designed to induce production of NO can promote neurogenesis. Two compounds have been employed, DETANONOate and SNAP, these compounds have successfully induced neurogenesis and improved functional outcome after stroke. The compound used likely crosses the blood brain barrier. Neurogenesis is a major last goal in neuroscience research. Developing a way to promote production of neurons opens up the opportunity to treat a wide variety of neurological disease, CNS injury and neurodegeneration. It is possible to augment the production of neurons in non-damaged brain, so as to increase function.

The market for a class of drugs that promotes the production of neurons is vast. Nitric oxide donors, of which DETANONO is but one example, promote neurogenesis. Increasing neurogenesis translates into a method to increase, improve neurological, behavioral and cognitive function, with age and after injury or disease.

The above discussion provides a factual basis for the use of nitric oxide to promote neurogenesis. The methods used with and the utility of the present invention can be shown by the following non-limiting examples and accompanying figures.

Methods:

General methods in molecular biology: Standard molecular biology techniques known in the art and not specifically described were generally followed as in Sambrook et al., *Molecular Cloning: A Laboratory Manual*, Cold Spring Harbor Laboratory Press, New York (1989), and in Ausubel et al., *Current Protocols in Molecular Biology*, John Wiley and Sons, Baltimore, Md. (1989) and in Perbal, *A Practical Guide to Molecular Cloning*, John Wiley & Sons, New York (1988), and in Watson et al., *Recombinant DNA*, Scientific American Books, New York and in Birren et al (eds) *Genome Analysis: A Laboratory Manual Series, Vols. 1–4* Cold Spring Harbor Laboratory Press, New York (1998) and methodology as set forth in U.S. Pat. Nos. 4,666,828; 4,683,202; 4,801,531; 5,192,659 and 5,272,057 and incorporated herein by reference. Polymerase chain reaction (PCR) was carried out generally as in *PCR Protocols: A Guide To Methods And Applications*, Academic Press, San Diego, Calif. (1990). In-situ (In-cell) PCR in combination with Flow Cytometry can be used for detection of cells containing specific DNA and mRNA sequences (Testoni et al, 1996, Blood 87:3822.)

General methods in immunology: Standard methods in immunology known in the art and not specifically described are generally followed as in Stites et al.(eds), Basic and Clinical Immunology (8th Edition), Appleton & Lange, Norwalk, Conn. (1994) and Mishell and Shiigi (eds), Selected Methods in Cellular Immunology, W.H. Freeman and Co., New York (1980).

Delivery of Therapeutics:

The compound of the present invention is administered and dosed in accordance with good medical practice, taking into account the clinical condition of the individual patient, the site and method of administration, scheduling of administration, patient age, sex, body weight and other factors known to medical practitioners. The pharmaceutically "effective amount" for purposes herein is thus determined by such considerations as are known in the art. The amount must be effective to achieve improvement including but not limited to improved survival rate or more rapid recovery, or improvement or elimination of symptoms and other indicators as are selected as appropriate measures by those skilled in the art.

In the method of the present invention, the compound of the present invention can be administered in various ways. It should be noted that it can be administered as the compound or as pharmaceutically acceptable salt and can be administered alone or as an active ingredient in combination with pharmaceutically acceptable carriers, diluents, adjuvants and vehicles. The compounds can be administered orally, subcutaneously or parenterally including intravenous, intraarterial, intramuscular, intraperitoneally, and intranasal administration as well as intrathecal and infusion techniques. Implants of the compounds are also useful. The patient being treated is a warm-blooded animal and, in particular, mammals including man. The pharmaceutically acceptable carriers, diluents, adjuvants and vehicles as well as implant carriers generally refer to inert, non-toxic solid or liquid fillers, diluents or encapsulating material not reacting with the active ingredients of the invention.

It is noted that humans are treated generally longer than the mice or other experimental animals exemplified herein which treatment has a length proportional to the length of the disease process and drug effectiveness. The doses may be single doses or multiple doses over a period of several days, but single doses are preferred.

The doses may be single doses or multiple doses over a period of several days. The treatment generally has a length proportional to the length of the disease process and drug effectiveness and the patient species being treated.

When administering the compound of the present invention parenterally, it will generally be formulated in a unit dosage injectable form (solution, suspension, emulsion). The pharmaceutical formulations suitable for injection include sterile aqueous solutions or dispersions and sterile powders for reconstitution into sterile injectable solutions or dispersions. The carrier can be a solvent or dispersing medium containing, for example, water, ethanol, polyol (for example, glycerol, propylene glycol, liquid polyethylene glycol, and the like), suitable mixtures thereof, and vegetable oils.

Proper fluidity can be maintained, for example, by the use of a coating such as lecithin, by the maintenance of the required particle size in the case of dispersion and by the use of surfactants. Nonaqueous vehicles such a cottonseed oil, sesame oil, olive oil, soybean oil, corn oil, sunflower oil, or peanut oil and esters, such as isopropyl myristate, may also be used as solvent systems for compound compositions. Additionally, various additives which enhance the stability, sterility, and isotonicity of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. In many cases, it will be desirable to include isotonic agents, for example, sugars, sodium chloride, and the like. Prolonged absorption of the injectable pharmaceutical form can be brought about by the use of agents delaying absorption, for example, aluminum monostearate and gelatin. According to the present invention, however, any vehicle, diluent, or additive used would have to be compatible with the compounds.

Sterile injectable solutions can be prepared by incorporating the compounds utilized in practicing the present invention in the required amount of the appropriate solvent with various of the other ingredients, as desired.

A pharmacological formulation of the present invention can be administered to the patient in an injectable formulation containing any compatible carrier, such as various vehicle, adjuvants, additives, and diluents; or the compounds utilized in the present invention can be administered parenterally to the patient in the form of slow-release subcutaneous implants or targeted delivery systems such as monoclonal antibodies, vectored delivery, iontophoretic, polymer matrices, liposomes, and microspheres. Examples of delivery systems useful in the present invention include: U.S. Pat. Nos. 5,225,182; 5,169,383; 5,167,616; 4,959,217; 4,925,678; 4,487,603; 4,486,194; 4,447,233; 4,447,224; 4,439,196; and 4,475,196. Many other such implants, delivery systems, and modules are well known to those skilled in the art.

A pharmacological formulation of the compound utilized in the present invention can be administered orally to the patient. Conventional methods such as administering the compounds in tablets, suspensions, solutions, emulsions, capsules, powders, syrups and the like are usable. Known techniques which deliver it orally or intravenously and retain the biological activity are preferred.

In one embodiment, the compound of the present invention can be administered initially by intravenous injection to bring blood levels to a suitable level. The patient's levels are then maintained by an oral dosage form, although other forms of administration, dependent upon the patient's condition and as indicated above, can be used. The quantity to be administered will vary for the patient being treated and will vary from about 100 ng/kg of body weight to 100 mg/kg of body weight per day and preferably will be from 10 mg/kg to per day.

EXAMPLES

Example 1

A pharmacological method to promote neurogenesis in brain was developed. Male Wistar rats were subjected to middle cerebral artery (MCA) occlusion by means of intraarterial placement of a clot at the origin of the right MCA. Animals were administered (iv/ip) nitric oxide donor compounds (DETANONO) after induction of stroke, at 24 and 48 hours (Group 1), or at 24 hours followed by daily injection (ip) of NO donor compound (Group 2). BrdU, a thymidine analog which identifies the formation of new cells, was injected (ip) daily over a period of 14 days from the onset of ischemia. Identification of cell type was determined by labeling immunoreactivity of specific cell proteins. Thus, neurons were identified by expression of NeuN, MAP2 and the astrocytes formed by GFAP. Measurements of neurogenesis were performed within specific regions of brain, the subventricular zone and the dentate gyrus.

Results: The data showed a significant increase in the numbers of BrdU positive cells in rats treated with DETANONO compared to those found in the untreated group. For Group 2, the results were as follows: subventricular zone: 2748±326 vs. 1653±91.4, dentate gyrus: granule cell layer, 135±18.9 vs. 37.3±3.6; 53.7±6.3 vs. 34.9±2.8, hilus, 43.8±10.2 vs. 10.1±2.4. For Group 1, a significant increase in BrdU cells in the granule cell layer was detected 89.5±12 vs. 37.3±3.6 in treated vs. non-treated rats, respectively. The vast majority of newly formed cells (>90%) within the dentate gyrus were neurons. In other areas of the brain, newly formed cells had glial and astrocytic phenotype.

Treatment of non-ischemic brain with DETANONO: Rats not subjected to any surgical procedures were treated with DETANONO. The drug was administered as a single dose (iv 0.12 mg). BrdU was injected daily for 14 days after treatment. One population (Group 3) of rats was sacrificed on the last day of BrdU injection. Another population (Group 4) was sacrificed at four weeks after the last BrdU injection. Animals which were not administered DETA-NONO were given BrdU with the identical protocol as that for the DETA-NONO treated rats (Group 5).

Results of Group 3 versus Group 5 were as follows: In the subventricular zones the results were respectively, 2952±102.6 vs. 1432.6±104.6; 2725.3±115.5 vs. 1655±9±102.9 in the dentate gyrus (granule cell layer) 73.7±8.11 vs. 39.9±7.26. In Group 4 versus Group 5, in the subventricular zone the results were as follows: 456.5±42.3 vs. 214.6±67.9; 518.4±67.2 vs. 233.1±49.2, respectively; in the dentate gyrus (hilus) 7.71±89 vs. 3.23±1.22, respectively. Rats treated with DETANONO exhibited a significant increase in newly formed cells, at both time points compared to non treated rats. Increases in newly formed cells were apparent in the subventricular zone and in the hippocampus. BrdU reactive cells were double labeled with neuronal markers NeuN and MAP2, and an astrocytic marker, GFAP. Newly formed cells exhibited neuronal or astrocytic proteins.

FIG. 1 shows double labeling immunohistochemistry within the hippocampus for BrdU and neuronal markers, NeuN and MAP2, and BrdU with the astrocytic marker, and GFAP in rats treated with DETANONO and subjected to strokes. Cells exhibited immunoreactivity to both markers, indicating both neuronal and astrocytic phenotype of the newly formed cells. It is estimated that more than 90% of the newly formed cells within the hippocampus are neuronal phenotype.

These data indicate that administration of a NO donor promotes neurogenesis in ischemic brain. This approach is applicable to many forms of CNS pathology and injury. In addition, NO also promotes neurogenesis in "normal" adult brain.

The purpose of the present invention is to promote an improved outcome from ischemic cerebral injury, or other neuronal injury, by inducing neurogenesis. Patients suffer neurological and functional deficits after stroke, CNS injury and neurodegenerative disease. These findings provide a means to enhance brain compensatory mechanism to improve function after CNS damage or degeneration. The induction of neurons will promote functional improvement after stroke.

Nitric oxide administered at propitious times after CNS injury promotes neurogenesis in brain and is able to facilitate neurogenesis. The mechanism for such production is that NO activates glutamate receptors. These glutamate receptors promote long term potentiation and subsequently induce regeneration of neurons. As an initial experiment, DETA/NO was employed, a compound with a long half-life (~50 hours) which produces NO. Increased numbers of new neurons were identified when this compound was administered at and beyond 24 hours after onset of stroke.

The experimental data included herein show that a pharmacological intervention designed to induce production of NO can promote neurogenesis. The compound used likely crosses the blood brain barrier. Neurogenesis is a major last goal in neuroscience research. Developing a way to promote production of neurons opens up the opportunity to treat a wide variety of neurological disease, CNS injury and neurodegeneration. It is possible to augment the production of neurons in non-damaged brain, so as to increase function.

The market for a class of drugs that promotes the production of neurons is vast. Nitric oxide donors, of which DETANONO is but one example, promote neurogenesis. Increasing neurogenesis translates into a method to increase, improve neurological, behavioral and cognitive function, with age and after injury or disease.

There have previously been no applications of NO donors, or this drug in particular, to the induction of neurogenesis after stroke.

Adult rodent brain is capable of generating neuronal progenitor cells in the subventricular zone (SVZ) and in the dentate gyrus of the hippocampus throughout the life of the animal. However, signals that regulate progenitor cell proliferation and differentiation are not known. Nitric oxide (NO) is a chemical messenger in biological systems and serves as a neurotransmitter in the brain. In the present study, the effects of NO on the proliferation of neuronal progenitor cells in the SVZ and in the dentate gyrus of adult rats was explored.

Two experiments were performed. In the first experiment, the effects of NO on the proliferation of neuronal progenitor cells in the SVZ and the dentate gyrus of non ischemic adult rats were examined. In the second experiment, the effects of NO on the proliferation of neuronal progenitor cells in the SVZ and in the dentate gyrus of ischemic adult rats were examined.

Male Wistar rats weighing 300–350 g were used in the present studies (Charles River Breeding Company, Wilmington, Mass.). DETANONOate, an NO donor with a half-life 20 hours under physiological conditions, was purchased from ALEXIS Biochemical Corporation. Bromodeoxyuridine (BrdU), the thymidine analog used as mitotic labeling, was purchased from Sigma Chemical. A mouse monoclonal antibody against BrdU was purchased from Boehringer Mannheim.

Male Wistar rats (n=28) weighing 300–350 g were anesthetized with halothane (1–3.5% in a mixture of 70% $N_2O$ and 30% $O_2$) using a face mask. The rectal temperature was maintained at 37±1° C. throughout the surgical procedure using a feedback regulated water heating system. The right femoral artery and vein were cannulated with a PE-50 catheter for continuous monitoring of blood pressure and measurement of blood gases (pH, $pO_2$, $pCO_2$) and for drug administration, respectively. DETANONOate was intravenously and intraperitoneally injected to rats.

DETANONO treatment: Rats were randomly divided into four groups. Group 1 (single Rx), rats were intravenously injected with four consecutive bolus doses of DETANONO (0.1 mg/kg each) every fifteen minutes (total dose of 0.4 mg/kg). Group 2 (two Rx group), rats were intravenously injected with four consecutive bolus doses of DETANONO (0.1 mg/kg each) every fifteen minutes (total dose 0.4 mg/kg) and rats received a second treatment at 24 hours later. Group 3 (seven Rx group), rats received four consecutive intravenous bolus doses of DETANONO (0.1 mg/kg each) every fifteen minutes on the first experimental day and rats were intraperitoneally injected with a bolus dose of DETANONO (0.4 mg/kg) daily for an additional six consecutive days. Group 4 (control), rats received saline only (single dose).

Rats received an intraperitoneal injection of BrdU (50 mg/kg) on the first day of DETANONO treatment and daily intraperitoneal injections of BrdU for fourteen consecutive days. To determine whether the proliferation and the differentiation of cells in the SVZ and dentate gyrus of adult rats is affected by NO, rats were sacrificed at fourteen days (n=3–5 per group) and 42 days (n=3–5 per group) after first dose of DETANONO treatment, respectively. Rats were transcardially perfused with 4% paraformaldehyde in 100 mM phosphate buffer, pH 7.4. Brains were removed and fixed in 4% formaldehyde.

For BrdU immunostaining, DNA was first denatured by incubating brain sections (6 μm) in 50% formamide 2×SSC at 65° C. for 2 hours and then in 2N HCl at 37° C. for 30 minutes. Sections were then rinsed with Tris buffer and treated with 1% of $H_2O_2$ to block endogenous peroxidase. Sections were incubated with a primary antibody to BrdU (1:100) at room temperature for one hour and then incubated with biotinylated secondary antibody (1:200, Vector, Burlingame, Calif.) for one hour. Reaction product was detected using 3'3'-diaminobenzidine-tetrahydrochloride (DAB, Sigma).

BrdU immunostained sections were digitized under 40× objectively (Olympus BX40) via the MCID computer imaging analysis system (Imaging Research, St. Catharines, Canada). BrdU immunoreactive nuclei were counted on a computer monitor to improve visualization and in one focal plane to avoid over-sampling. Structures were sampled either by selecting predetermined areas on each section (RMS and OB) or by analyzing entire structures on each section (dentate gyrus and SVZ).

Every 40th coronal section was selected from each rat for a total of seven sections between AP+10.6 mm, genu corpus callosum, and AP+8.74 mm-anterior commissure crossing (Paxinos and Watson, 1986). BrdU immunoreactive-positive nuclei were counted in the lateral ventricle wall. All BrdU immunoreactive-positive nuclei in these areas are presented as the number of the BrdU immunoreactive cells/$mm^2$. Density for the seven sections was averaged to obtain a mean density value for each animal.

Every 20th section was selected from each rat for a total of six sections from the sagittal series of the OB/frontal cortex. As depicted in FIG. 1, two predetermined areas (100×100 µm) in the RMS and four areas (300×300 µm) in the granule cell layer (GCL) of the OB were analyzed on each section. All BrdU positive nuclei in these selected areas are presented as the number of the cells/mm². BrdU density for the six sections was averaged to obtain a mean density value for each animal.

Each 50th coronal section was selected from each rat for a total of eight sections between AP+5.86 mm and AP+2.96 mm including the hilus, subgranular zone (SGZ), and inner first, second and third of the granule cell layer (GCL). The SGZ, defined as a two-cell body wide zone along the border of the GCL and the hilus, were always combined with the GCL for quantification. All BrdU immunoreactive nuclei in these areas are presented as the number of the BrdU immunoreactive cells/mm². Density for the eight sections was averaged to obtain a mean density value for each animal.

Results

Figure 2A:
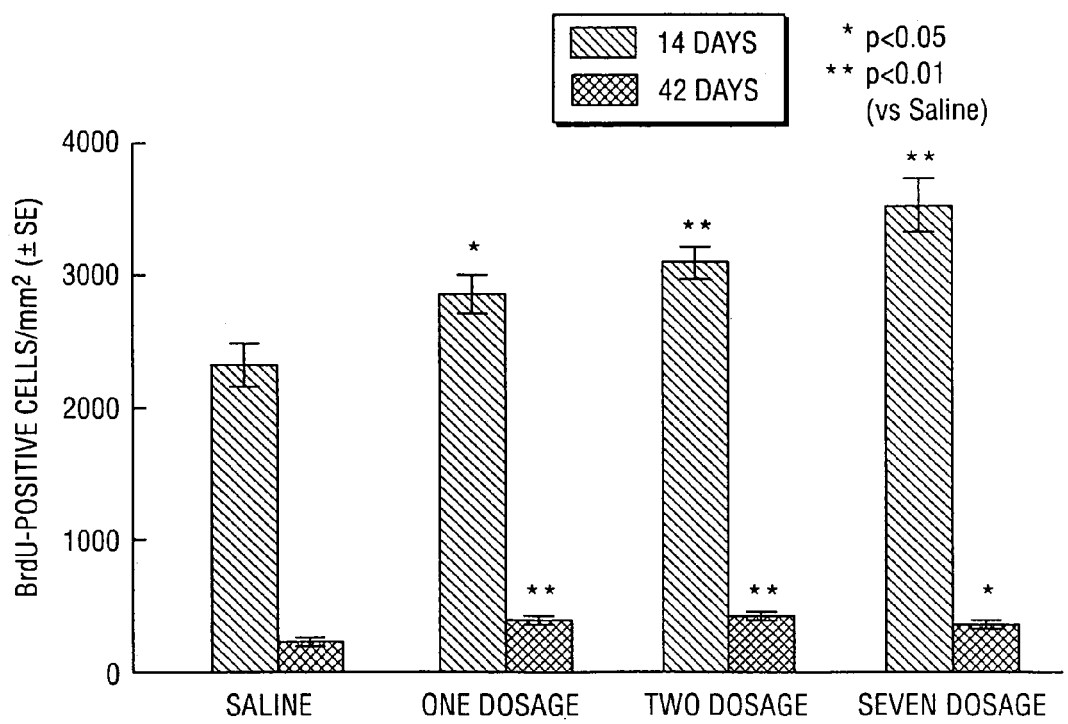
FIGS. 2A and 2B are graphs showing the amount of BrdU-positive cells in the subventricular zone (SVZ)
Figure 2B:
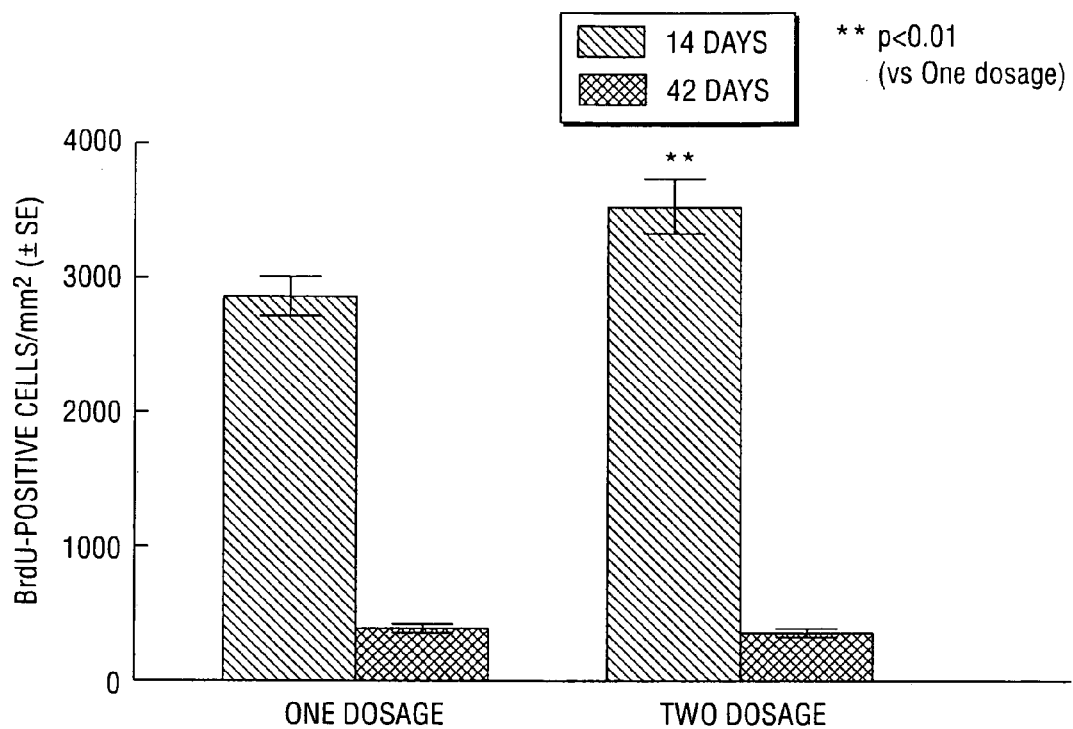

Rats treated with DEANONO have a significant ($p<0.05$) increase in numbers of BrdU immunoreactive cells in the SVZ compared with rats treated with saline at fourteen days and 42 days after treatment (FIG. 2a). Rats that received seven doses of DETANONO exhibited the highest number of BrdU immunoreactive cells compared with rats that received one and two doses of DETANONO at fourteen days after treatment. There was a significant difference in numbers of BrdU immunoreactive cells between one dose and seven doses of DETANONO was detected (FIG. 2b), suggesting that increases in BrdU immunoreactive cells is dose dependent manner. Although numbers of BrdU immunoreactive cells decreased at 42 days after treatment as compared with the number of cells at 14 days, the number of BrdU immunoreactive cells remained significantly increased compared with the number in control saline animals (FIG. 2a).

Numbers of BrdU immunoreactive cells did not significantly increase in the RMS in rats treated with DETANONO at fourteen days and 42 days after treatment (Table 1). However, significant increases in BrdU immunoreactive cells were detected in OB at 42 days after a single set of DETANONO treatment and at fourteen days and 42 days after two and seven sets of DETANONO treatment compared with the control group (Table 1), suggesting an increased migration of SVZ progenitors.

Figure 3:
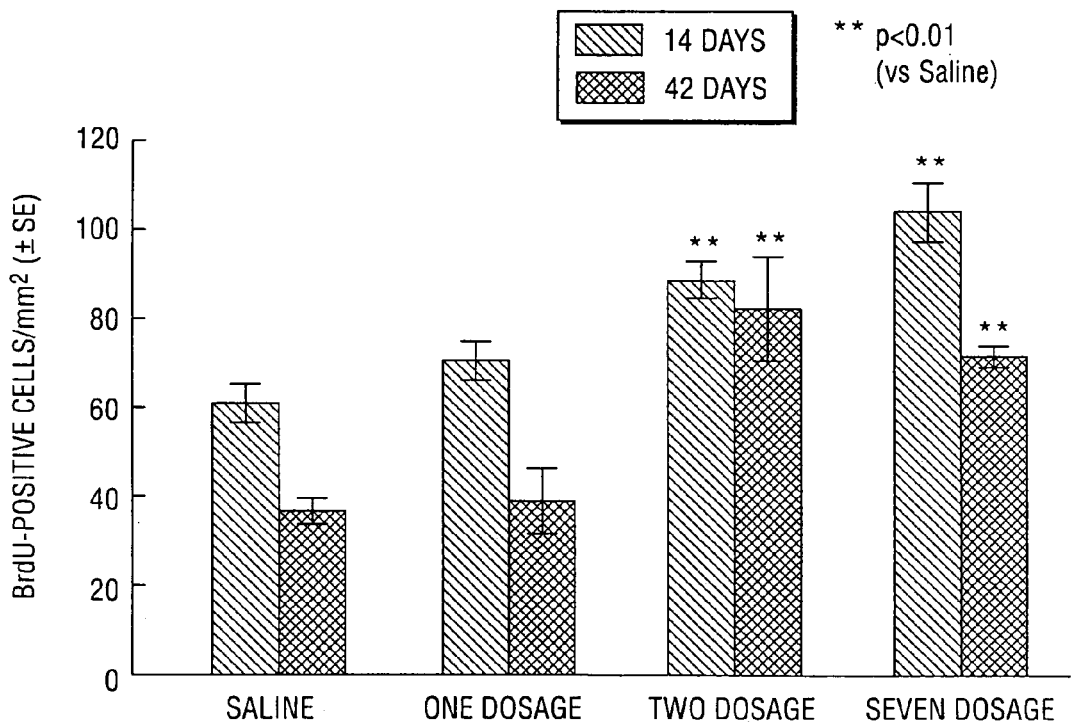
FIG. 3 is a graph showing the amount of BrdU-positive cells in the dentate gyrus.
Figure 4A:
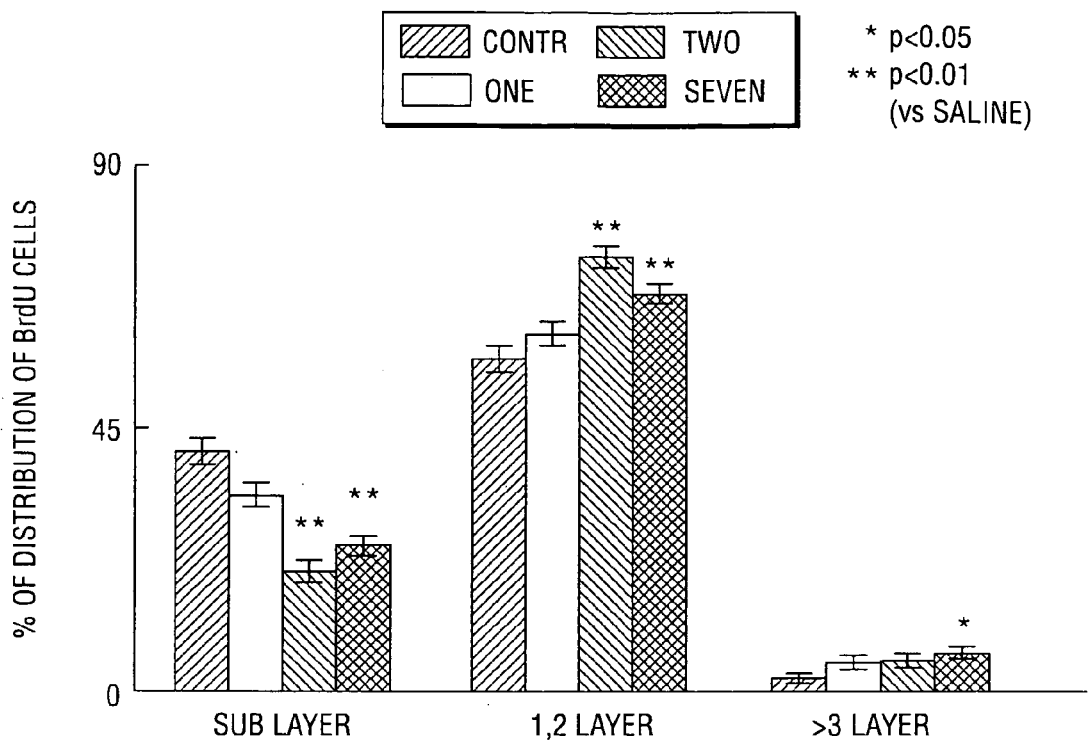
FIGS. 4A and 4B are graphs showing the percent of distribution of BrdU cells in the dentate gyrus.
Figure 4B:
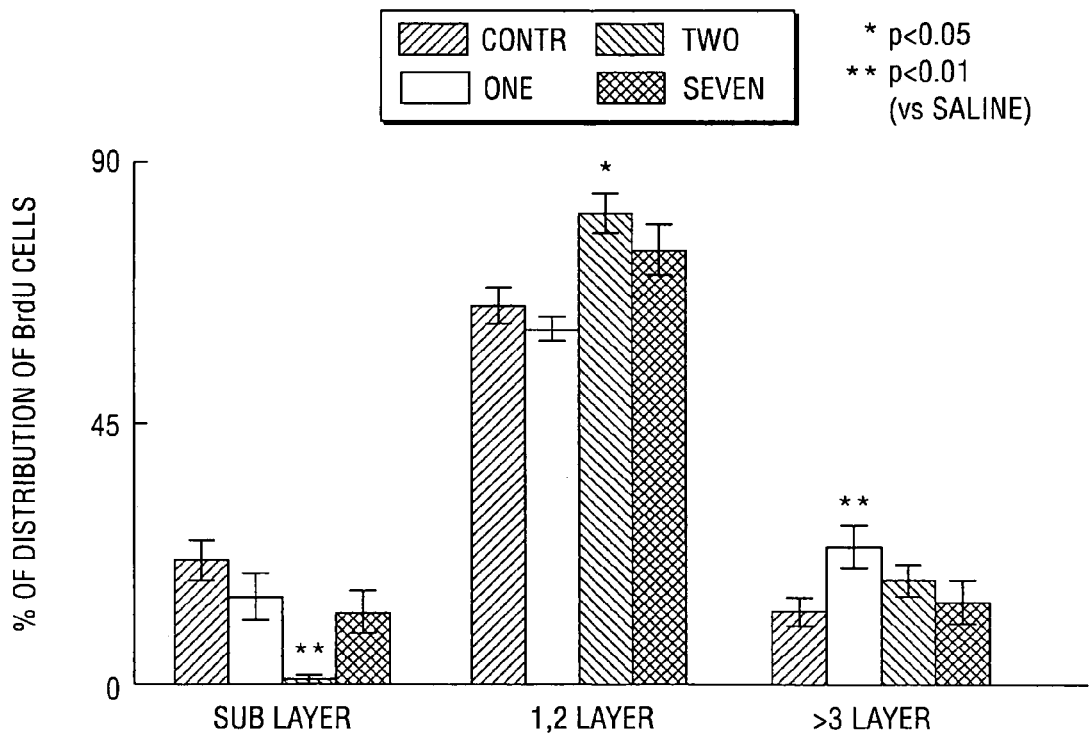
Figure 5:
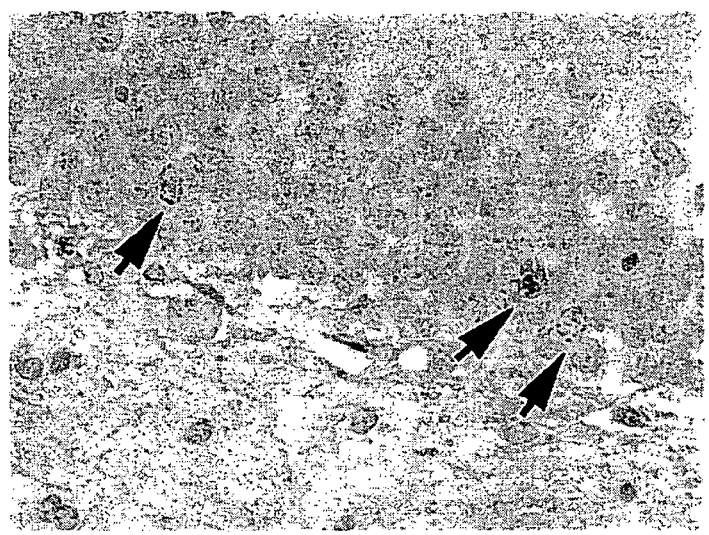
FIG. 5 is a photograph showing the size of BrdU immunoreactive cells in relation to granule cells in granule layers.

A single DETANONO treatment did not significantly increase in numbers of BrdU immunoreactive cells in the dentate gyrus at fourteen days and 42 days after treatment (FIG. 3). In contrast, rats treated with two and seven sets of DETANONO exhibited significant ($p<0.01$) increases in numbers of BrdU immunoreactive cells in the dentate gyrus at fourteen days and 42 days after treatment compared with the control group (FIG. 3). Percentage of distribution of BrdU immunoreactive cells in the dentate gyrus showed that treatment with DETANONO significantly decreases percentage of BrdU immunoreactive cells in subgranular zone and significantly increases in the granule layers at fourteen days and 42 days after treatment compared with the control group (FIGS. 4a and 4b), indicating that NO promote migration of BrdU immunoreactive cells. The BrdU immunoreactive cells were oval and rounded and either the same size or smaller than nuclei of the granule cells in granule layers (FIG. 5).

The data demonstrate that treatment with DETANONO to adult rats not only increases proliferation of SVZ and dentate gyrus progenitor cells but also prolongs survival of proliferated progenitor cells. Some BrdU immunoreactive cells have morphological characteristics of granule cells in the dentate gyrus. Thus, the data suggest that NO enhances neurogenesis in adult rat brain.

Based on above data, a second experiment was performed to explore NO effects on focal embolic cerebral ischemic brain. All procedures were the same as in the first experiment except for the following procedures.

Male Wistar rats (n=30) weighing 300–350 g were subjected to middle cerebral artery (MCA) occlusion. The MCA was occluded by placement of an embolus at the origin of the MCA. Briefly, a single intact fibrin rich 24 hour old homologous clot (about 1 µl) was placed at the origin of the MCA via a fifteen mm length of modified PE-50 catheter. The experimental protocol consisted of four groups. In Group I (control group), rats were subjected to MCA occlusion and received four consecutive intravenous bolus doses of saline (0.52 ml each, every fifteen minutes) at 24 hours after ischemia. Group II (DETNO/NO precondition) rats received four consecutive intravenous bolus doses of DETANONO (0.1 mg/kg each, every fifteen minutes, and total dose 0.4 mg/kg) at 24 hours before embolization. Group III (DETANONO two set group), animals received two consecutive intravenous bolus doses of DETANONO (0.1 mg/kg each, every fifteen minutes and total dose 0.4 mg/kg) at 24 and 48 hours after occlusion. Group IV (DETANONO seven set group), animals received four consecutive intravenous bolus doses of DETANONO (0.1 mg/kg each, every fifteen minutes and total dose 0.4 mg/kg) at 24 hours after embolization. Subsequently, rats were intraperitoneally injected with DETA/NO at 0.4 mg/kg every day for six consecutive days.

Embolic MCA occlusion resulted in significant ($p<0.05$) increases in numbers of BrdU immunoreactive cells in the ipsilateral SVZ and OB at fourteen days after MCA occlusion compared with non-ischemic rats (Table 2). The numbers of BrdU reactive cells decreased at 42 days after MCA occlusion, showing that focal cerebral ischemia induces transient increases in proliferation of progenitor cells in the ipsilateral SVZ (Table 2). MCA occlusion did not affect proliferation of progenitor cells in the contralateral SVZ and OB and in the both dentate gyrus (Table 2).

Figure 6A:
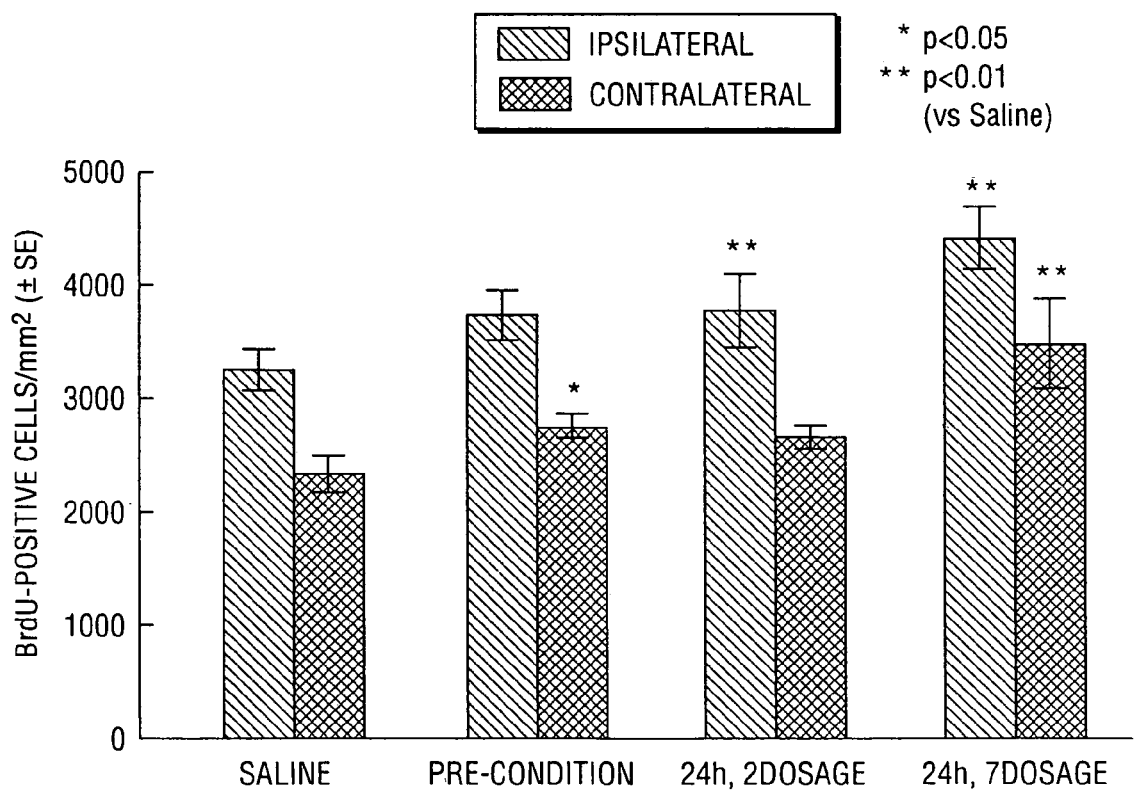
FIGS. 6A and 6B are graphs showing the amount of BrdU-positive cells in the SVZ.
Figure 6B:
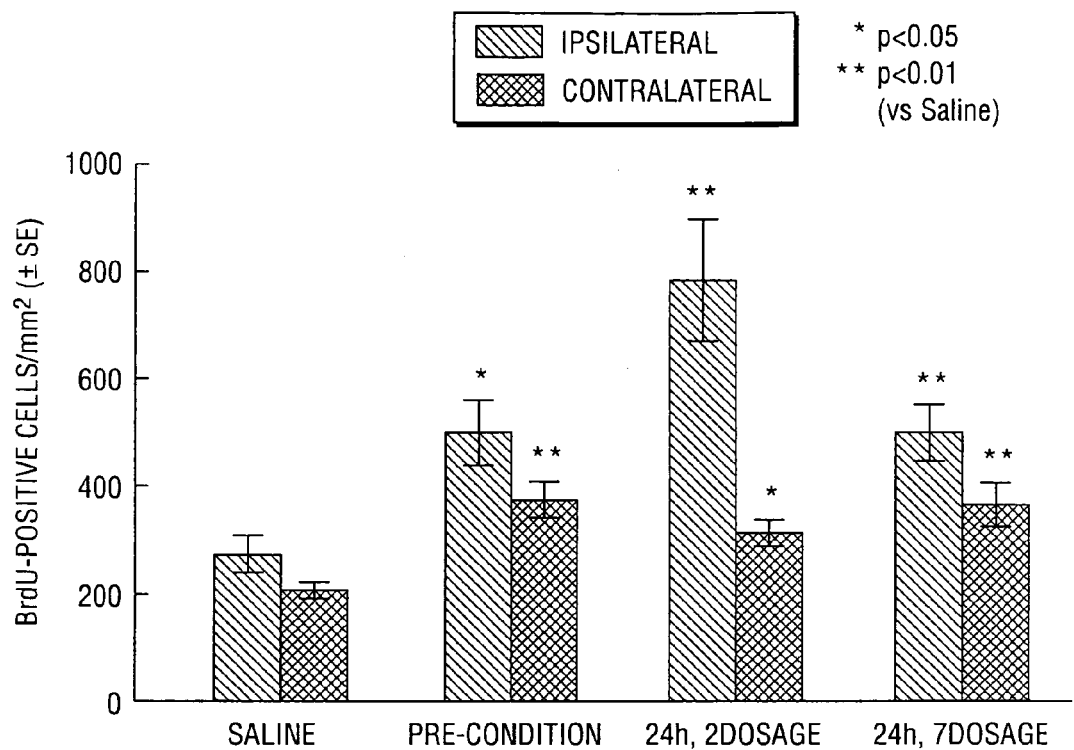

Significant ($p<0.05$) increases in numbers of BrdU immunoreactive cells were detected in the contralateral SVZ at 14 days after MCA occlusion and in both SVZs at 42 days after MCA occlusion in the preconditioned group compared with the non-treated MCA occlusion group (FIGS. 6A, 6B). Rats in two dosage groups had a significant increase in numbers of BrdU immunoreactive cells in the ipsilateral SVZ at 14 days and also had significant increases in numbers of BrdU immunoreactive cells in both SVZ at 42 days after MCA occlusion (FIGS. 6A, 6B). Rats treated with seven sets of DETANONO injection exhibited significant increases in BrdU immunoreactive cells in the contralateral and in the ipsilateral SVZ at 14 days and 42 days after MCA occlusion.

Figure 7A:
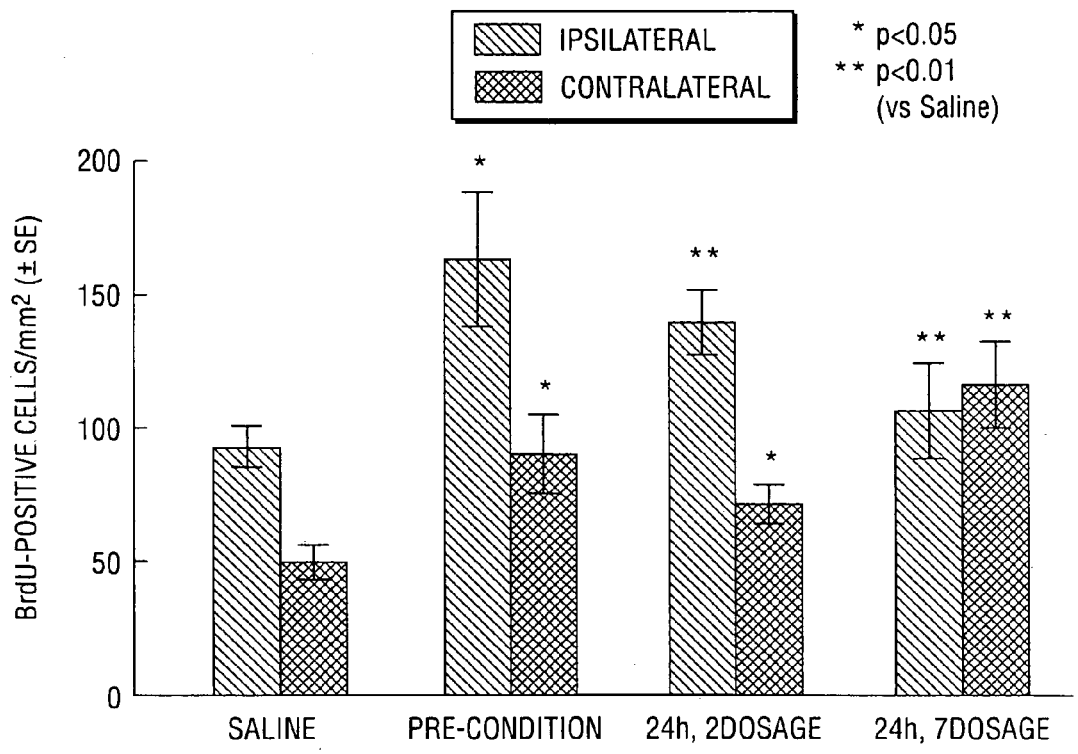
FIGS. 7A and 7B are graphs showing the amount of BrdU-positive cells in the olfactory bulb (OB)
Figure 7B:
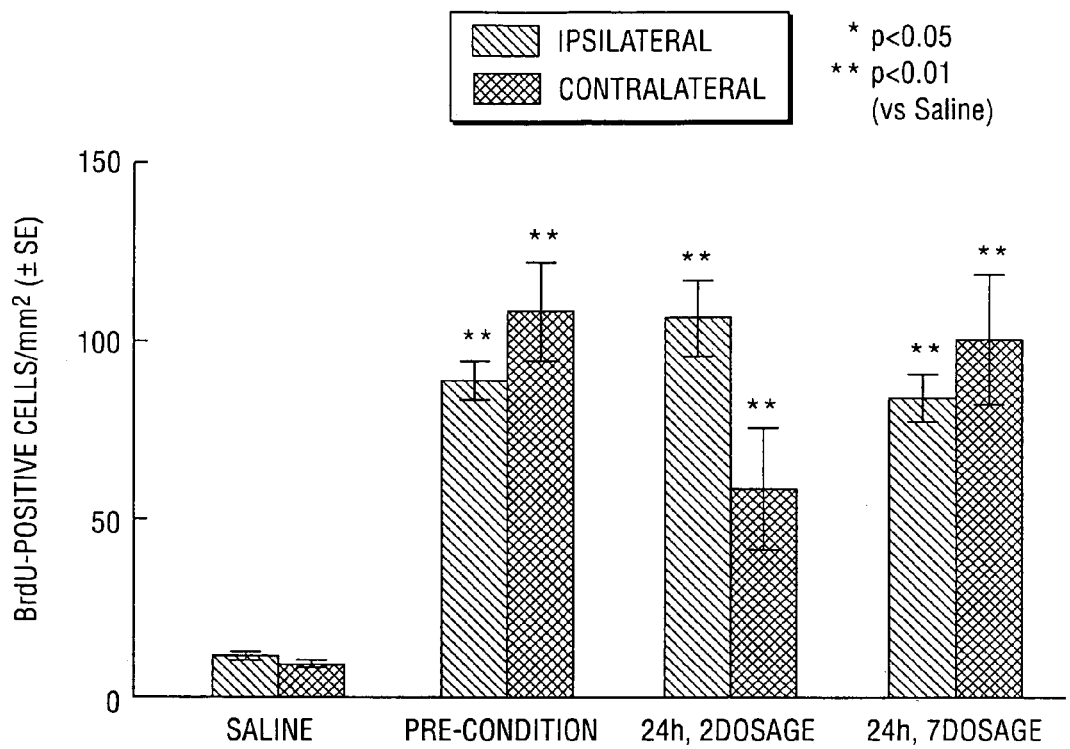

Significant increases in BrdU immunoreactive cells were detected in the OB in the ischemic rats treated with DETANONO at 14 days and 42 days after MCA occlusion (FIGS. 7A, 7B).

Figure 8A:
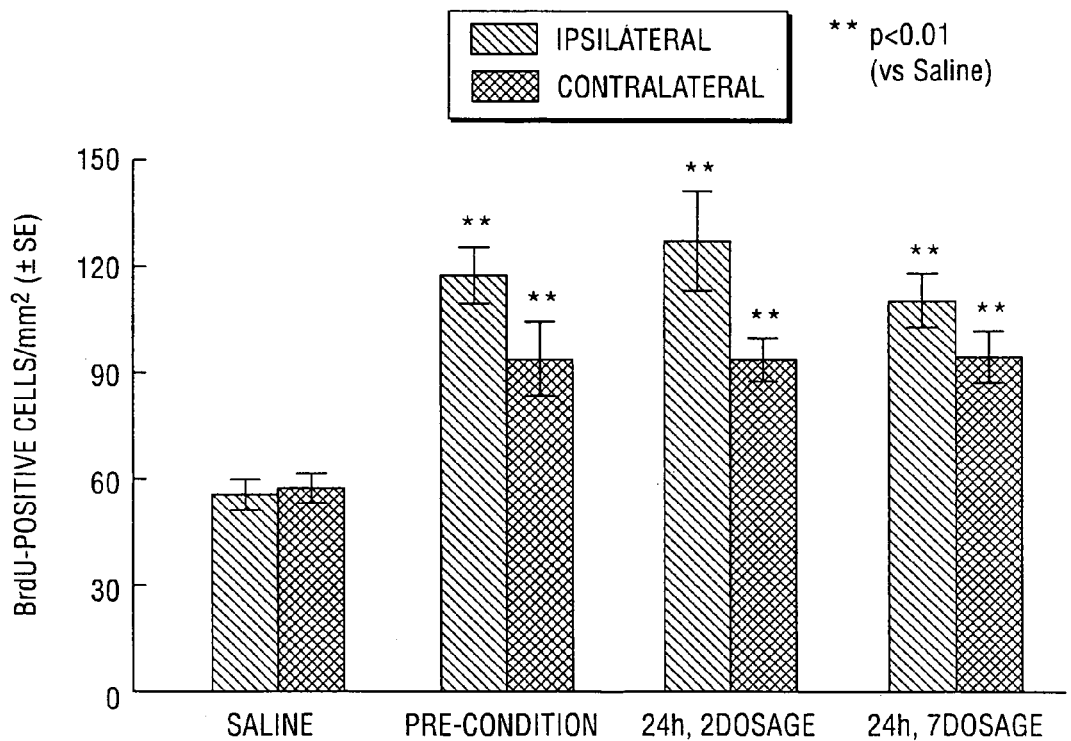
FIGS. 8A and 8B are graphs showing the amount of BrdU-positive cells in the dentate gyrus.
Figure 8B:
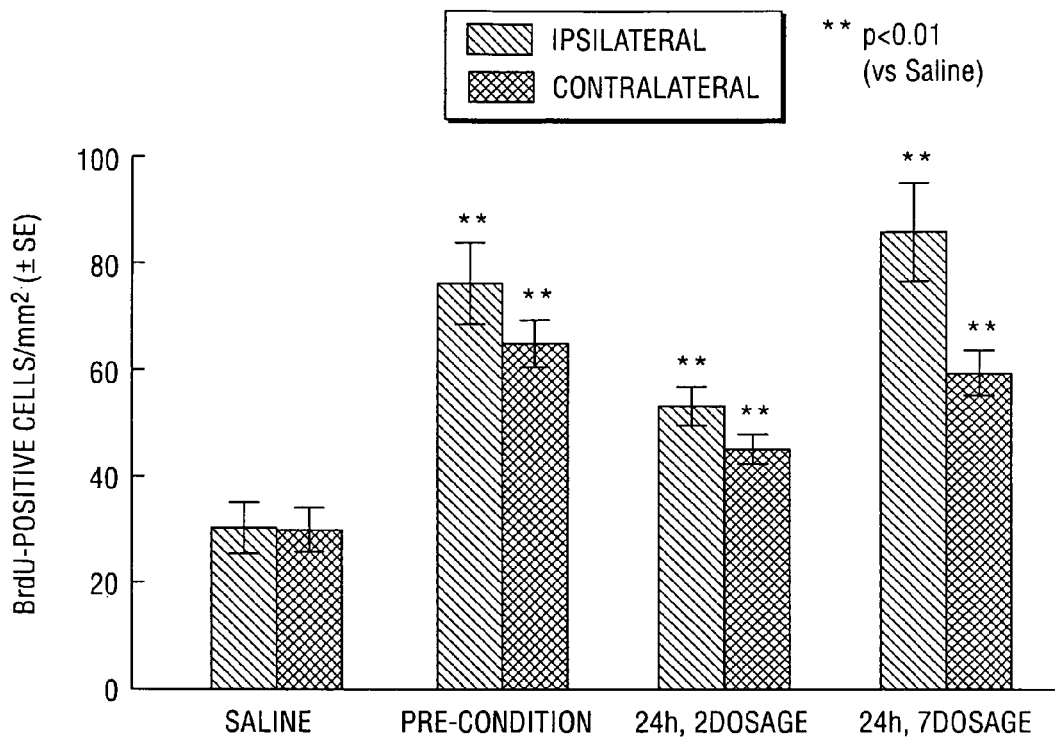

The ischemic rats treated with DETANONO had significant increases in BrdU immunoreactive cells in dentate gyrus at 14 days and 42 days after MCA occlusion compared with MCA occlusion group (FIGS. 8A, 8B).

Figure 9:
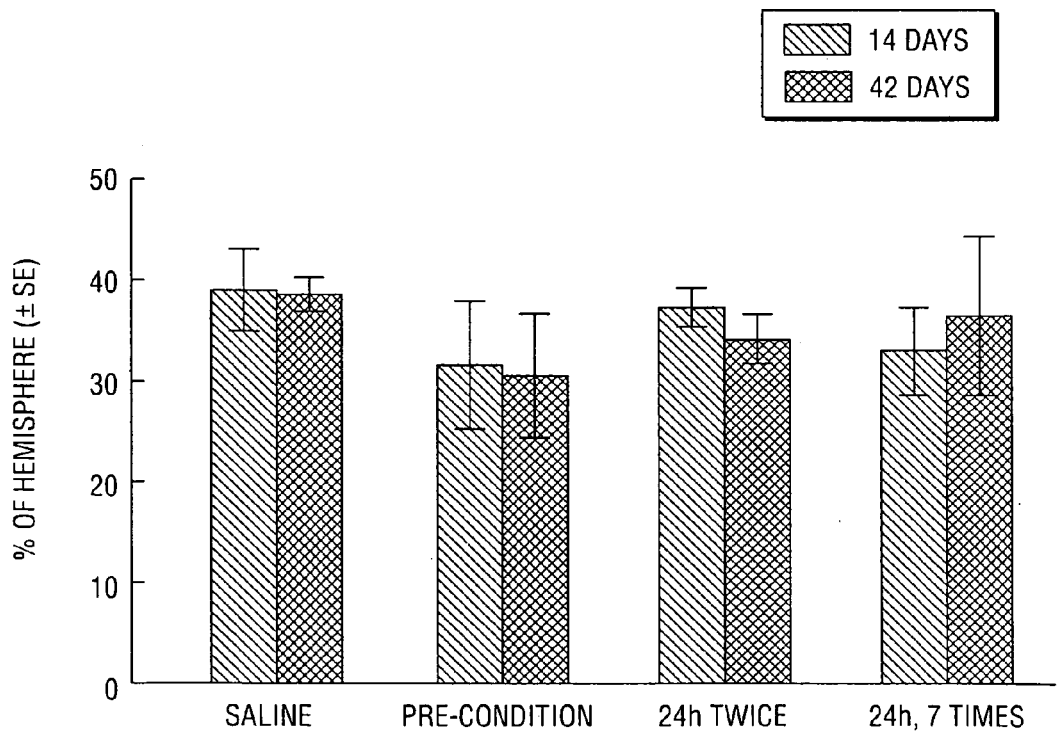
FIG. 9 is a graph showing a lesion volume study.

The ischemic rats treated with DETANONO did not exhibit a significant reduction of ischemic lesion volume (FIG. 9).

These data demonstrate that embolic MCA occlusion itself increases proliferation of progenitor cells in the ipsilateral SVZ. Many cells born in the SVZ migrate along RMS into the OB, where they differentiate into neurons. Thus, increases in the number of BrdU immunoreactive cells in the ipsilateral OB suggest an increased migration of the ipsilateral SVZ progenitor cells. These data also suggest that signals which increase proliferation of progenitor cells are transient and local after MCA occlusion. However, significant increases in proliferation of progenitor cells was sustained at least for 42 days after MCA occlusion when the ischemic rats were treated with DETANONO. Increases in proliferation of progenitor cells are induced by NO, since increases in numbers of BrdU immunoreactive cells involved not only both SVZ but also both dentate gyrus. However, there are differences in a number of BrdU cells between non-ischemic rats treated with DETANONO and the ischemic rats treated with DETANONO. The ischemic rats treated with DETANONO had higher absolute numbers of BrdU immunoreactive cells in the dentate gyrus at 14 days and 42 days after MCA occlusion than the numbers of non-ischemic rats treated with DETANONO, suggesting that NO may amplify signals generated by ischemia to increase proliferation of progenitor cells. Therefore, the data indicate that focal cerebral ischemia produces transient proliferation of progenitor cells and that NO enhances proliferation of progenitor cells in the ischemic brain.

Example 2

Administration of nitric oxide donor compound (DETA/NO) to normal and ischemic rats promotes neurogenesis in non-ischemic and ischemic brains. Since then, additional experiments have been performed to test the hypothesis that neurogenesis induced by DETA/NO promotes functional improvement after stroke; the data is provided herewith. Animals were administered (iv/ip) DETA/NO at one day (Group 1) or seven days (Group 2) after induction of stroke and followed by daily injection (ip) of DETA/NO over a period of seven days. Another NO donor compound (SNAP) was administered (iv) to ischemic rats at one day and two days after stroke (Group 3). Young (3 month old) rats were used in Groups 1 and 2. Middle aged rats (10 to 12 months old) were used in Group 3. A battery of neurological functional tests were measured from two days to forty-two days after stroke. These tests included 1) Neurological severity score (NSS) which measures motor, sensory and reflex functions and is similar to the contralateral neglect testing described in humans. The higher the score, the more severe the injury; 2) Rotarod test measures fore and hindlimb motor coordination and balance. Data are presented as percentage of baseline values; 3) Footfault test measures fore and hindlimb motor coordination. The higher the number, the more severe the injury; 4) Adhesive removal test measures sensorimotor impairments. Data are presented as time (seconds). The longer the time period, the more severe the injury; 5) Animal body weight.

Results

Figure 10:
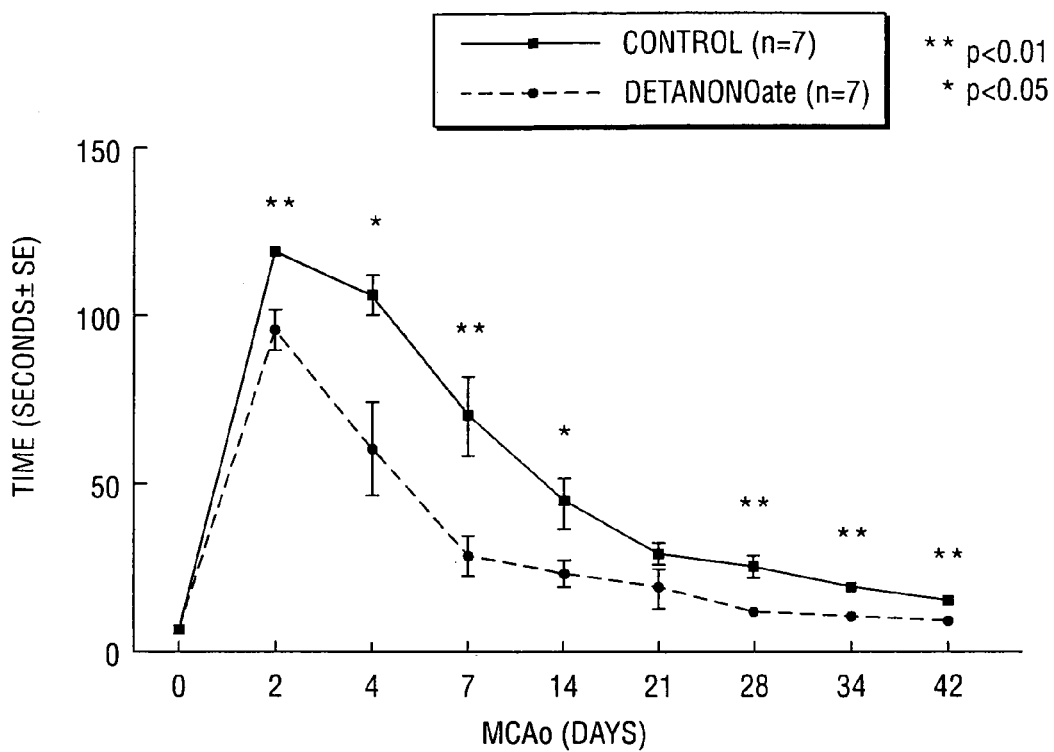
FIG. 10 is a graph showing in Time versus MCAo, the results of an adhesive removal test.
Figure 11:
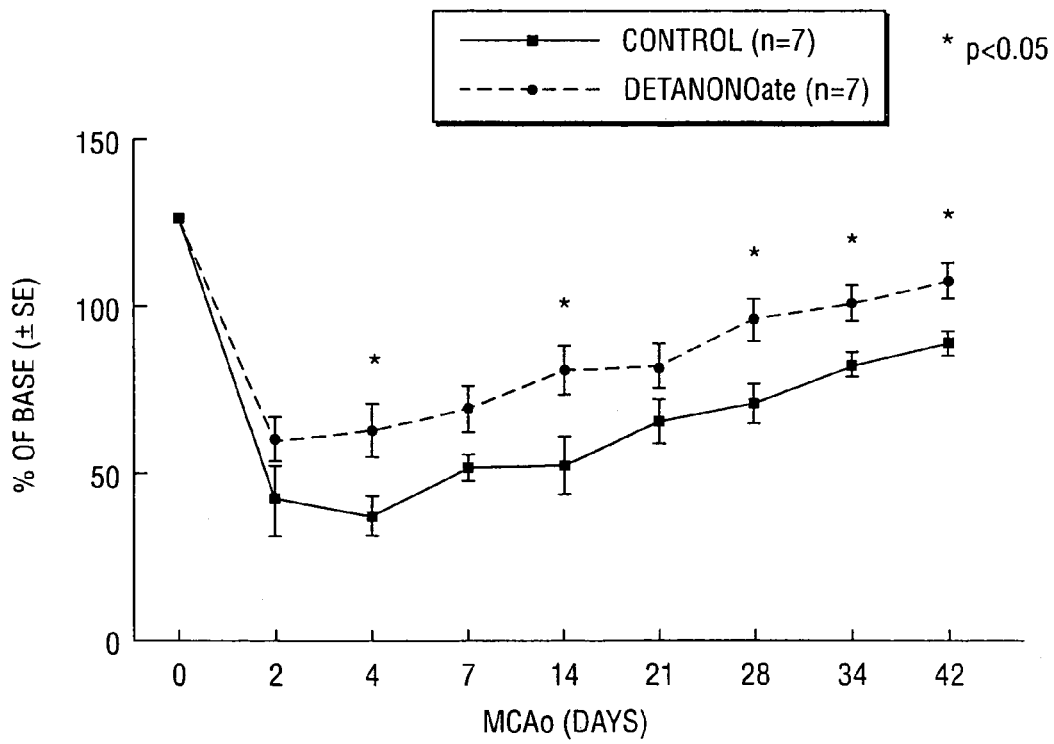
FIG. 11 is a graph showing the results of a Rotarod test.
Figure 12:
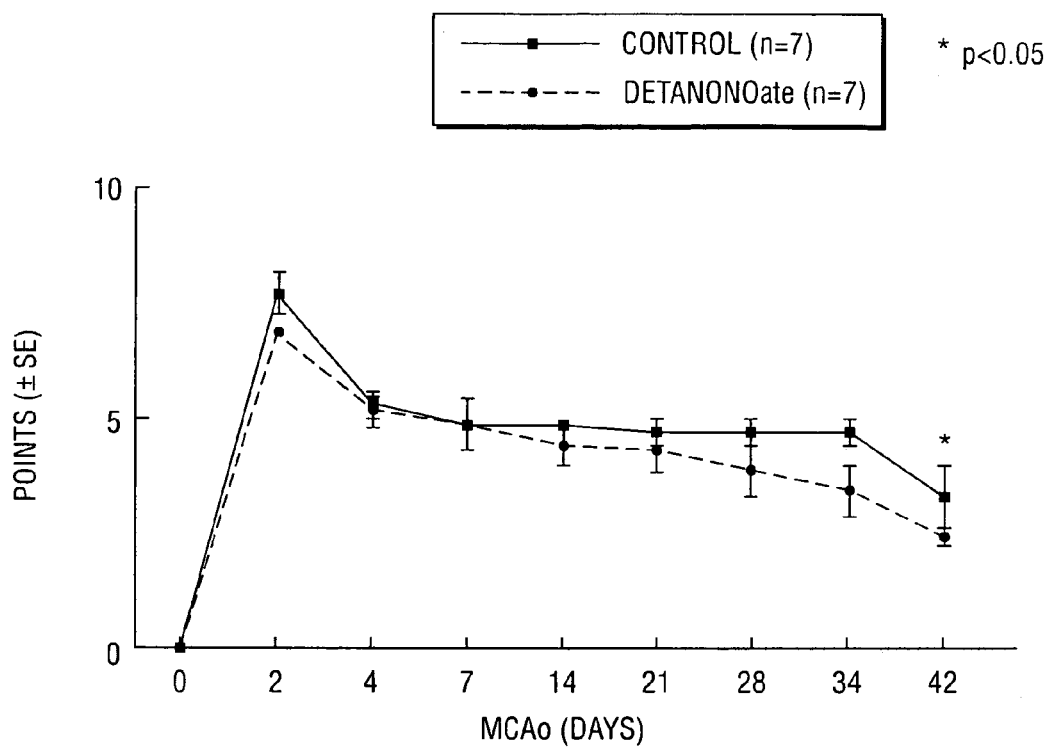
FIG. 12 is a graph showing the result of the NSS test.
Figure 13:
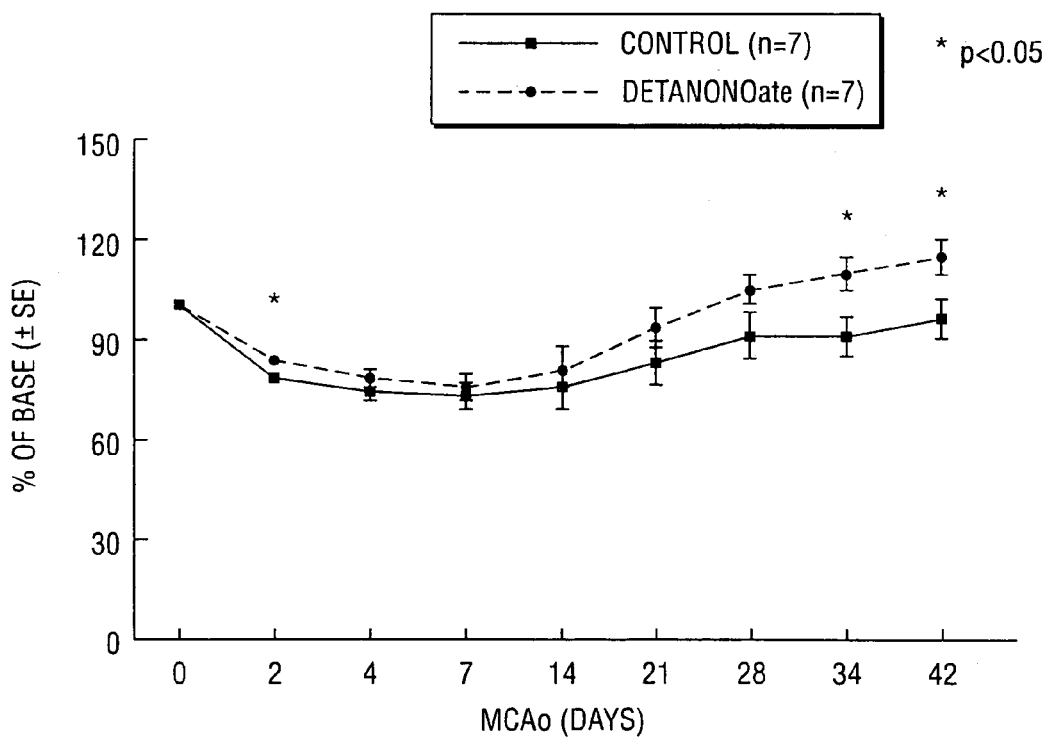
FIG. 13 is a graph showing the percent weight.

Group 1: Significant improvements on motor and sensorimotor functions (FIG. 10 Rotarod test, FIG. 11 Adhesive Removal test, FIG. 12 NSS test) and animal body weight (FIG. 13) were detected in rats treated with DETA/NO compared with control rats.

Figure 14:
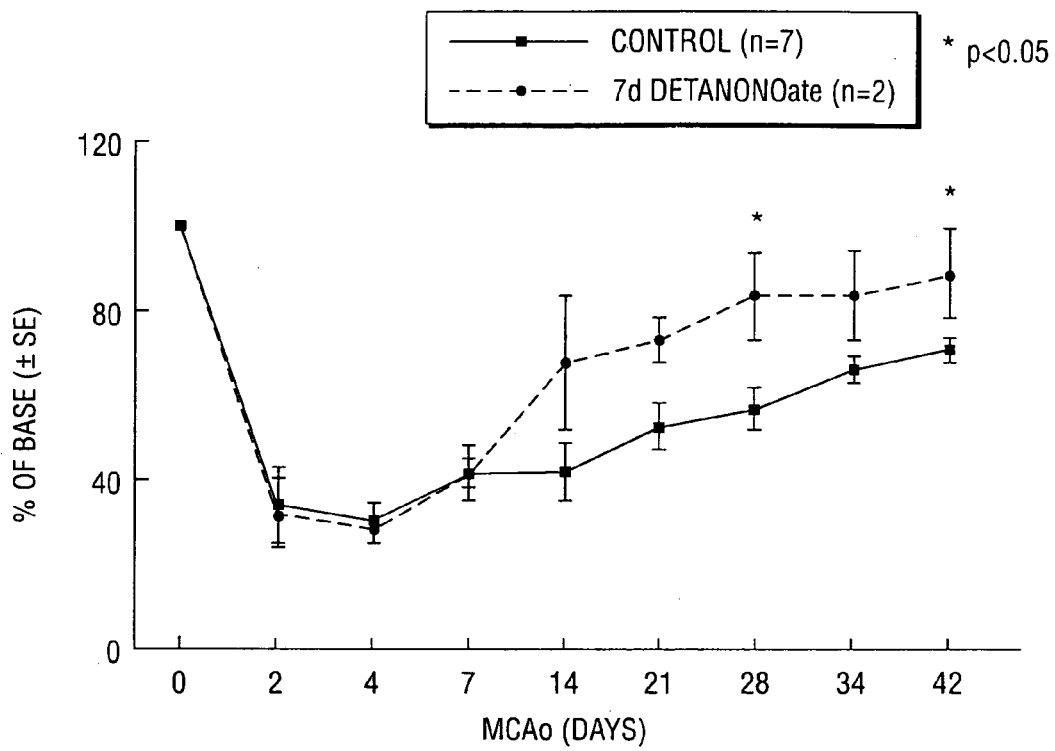
FIG. 14 is a graph showing the results of a Rotarod test.

Group 2: A significant improvement of neurological function was only detected in Rotarod test at 28 and 42 days after stroke (FIG. 14) compared with control animals.

Figure 15:
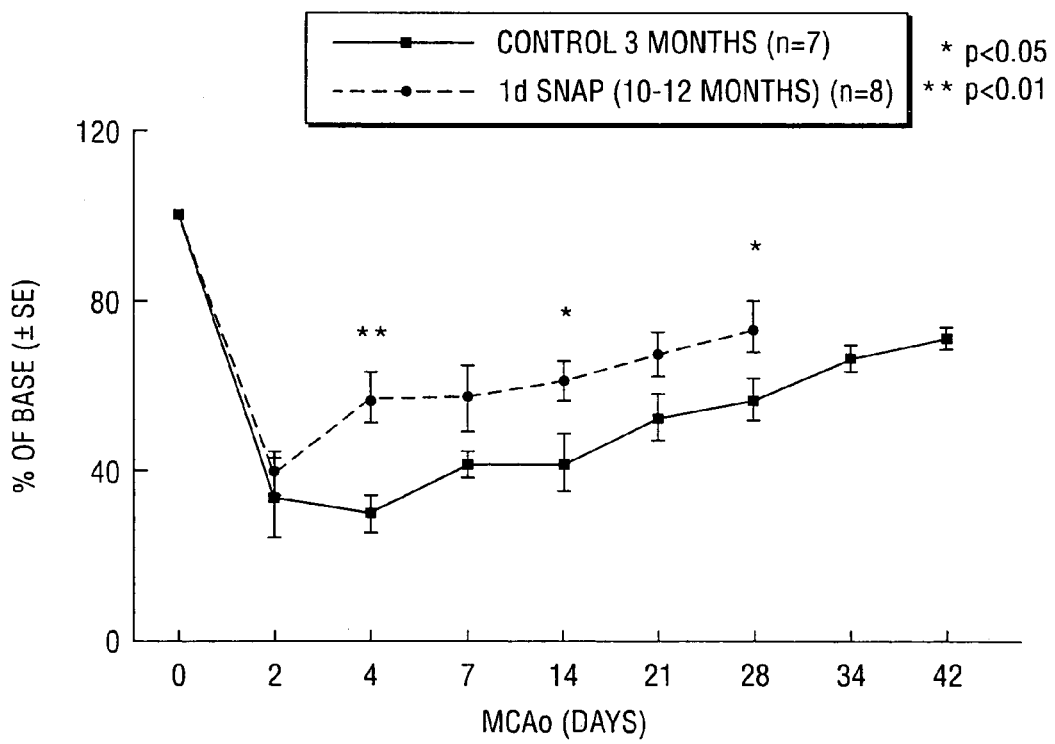
FIG. 15 is a graph showing further results of a Rotarod test
Figure 16:
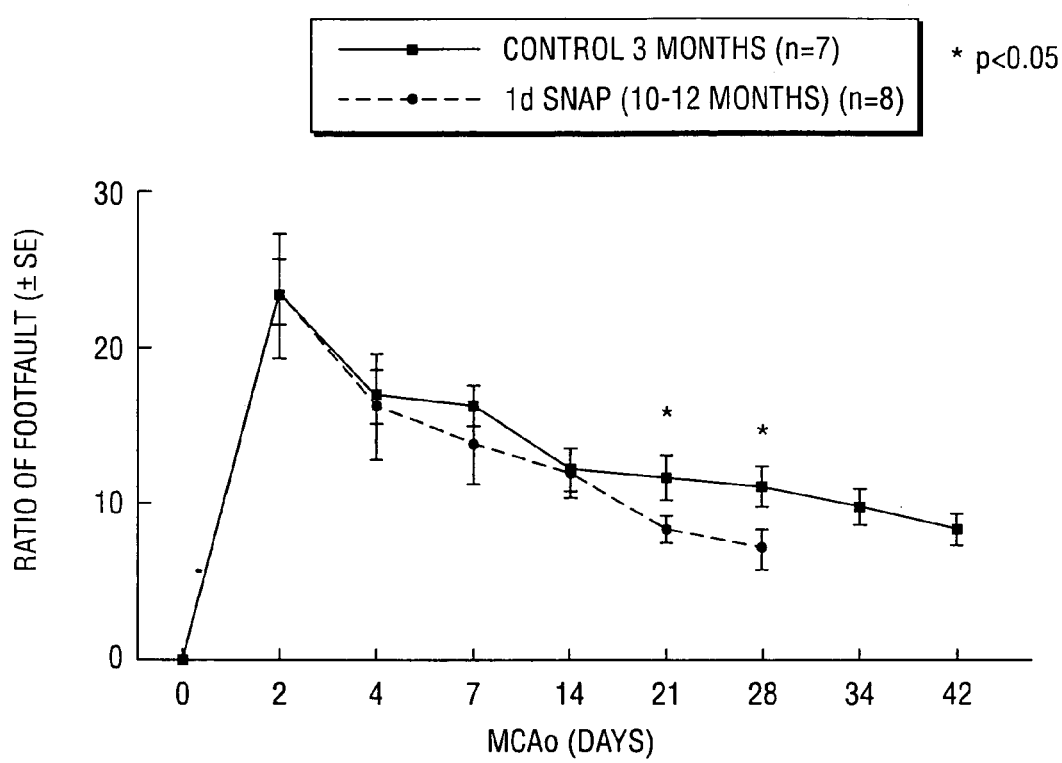
FIG. 16 is a graph showing the results of the footfault test.
Figure 17:
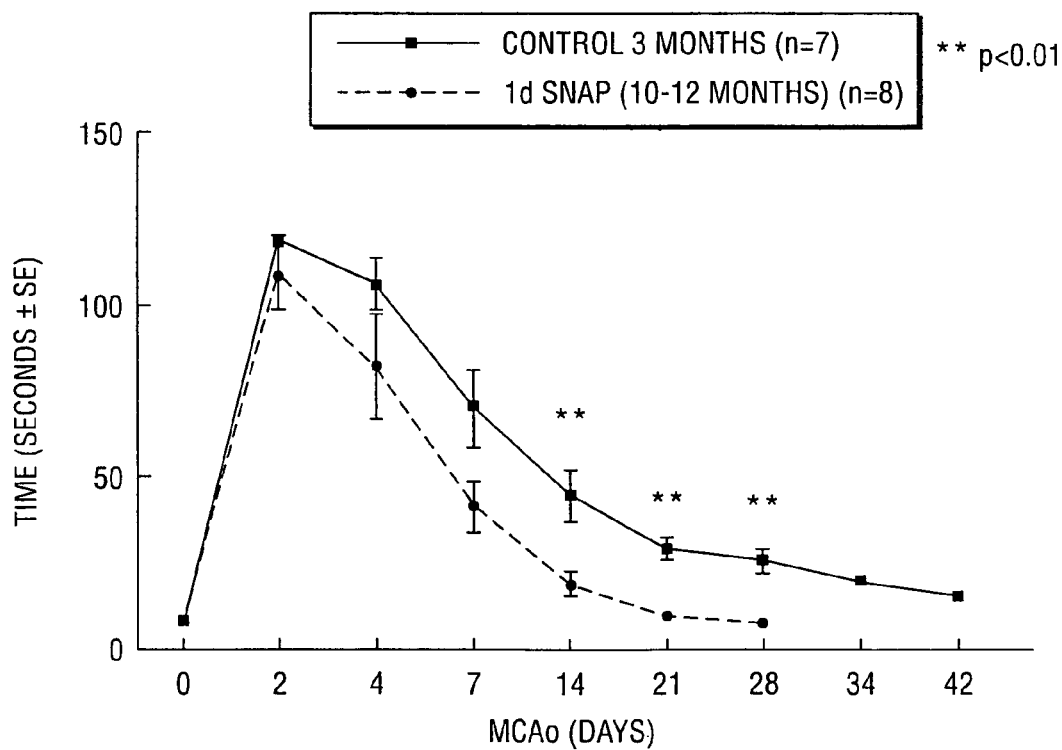
FIG. 17 is a graph showing the results of further adhesive removal tests.

Group 3: Animals treated with SNAP exhibited significant improvements on motor and sensorimotor functions (FIG. 15 Rotarod test, FIG. 16 footfault test, and FIG. 17 Adhesive removal test) compared with control animals.

CONCLUSIONS

These data indicate 1) administration of DETANONO to ischemic rats improves neurological functional recovery and these improvements can be achieved even when DETANONO is administered seven days after stroke; 2) in addition to DETANONO, administration of SNAP to ischemic rats also improves neurological functions, suggesting that administration of NO donor compounds can enhance functional recovery; and 3) administration of SNAP to middle aged rats is effective to promote functional recovery, which is important and clinically relevant because most stroke patients are middle age and older. These data, together with previous data showing that NO donor promotes neurogenesis, suggest that NO donor compounds enhance neurological functional recovery after stroke via promotion of neurogenesis in ischemic brain.

Throughout this application, various publications, including United States patents, are referenced by author and year and patents by number. Full citations for the publications are listed below. The disclosures of these publications and patents in their entireties are hereby incorporated by reference into this application in order to more fully describe the state of the art to which this invention pertains.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the described invention, the invention may be practiced otherwise than as specifically described.

TABLE 1

Density of newborn cells in the brain

| Area | Saline | DETA NO ONCE | DETA NO TWICE | DETA NO × 7 TIMES |
| --- | --- | --- | --- | --- |
| Rostral migratory stream (BrdU 50 mg/kg ip daily × 14 d) | | | | |
| 1 day after last BrdU injection (14 d) Right side | 869.2 ± 98.25 | 950.25 ± 99.55 | 991 ± 98.25 | 1169.4 ± 218.85 |
| 1 day after last BrdU injection (14 d) Left side | 841.9 ± 230.4 | 998.55 ± 59.7 | 1070.85 ± 160.1 | 1312.5 ± 265 |

TABLE 1-continued

Density of newborn cells in the brain

| Area | Saline | DETA NO ONCE | DETA NO TWICE | DETA NO × 7 TIMES |
|---|---|---|---|---|
| 4 weeks after last BrdU injection Right side | 21.85 ± 6.55 | 22.5 ± 5.95 | 32.9 ± 8.15 | 45 ± 11.35 |
| 4 weeks after last BrdU injection Left side | 21.2 ± 5.2 | 26.25 ± 6.9 | 37.8 ± 5.15 | 47.5 ± 15.6 |
| Olfactory bulb (BrdU 50 mg/kg ip daily × 14 d) | | | | |
| 1 day after last BrdU injection (14 d) Ipsilateral | 45.15 ± 7.4 | 41.4 ± 5.55 | 91.65 ± 12.35* | 106.25 ± 17.7** |
| 1 day after last BrdU injection (14 d) Contralateral | 31.55 ± 8.45 | 39.75 ± 6.2 | 99.6 ± 10.5** | 116.55 ± 16.45** |
| 4 weeks after last BrdU Injection (42 d) Ipsilateral | 12.95 ± 2.6 | 75.65 ± 10.85** | 85 ± 15.95** | 84.4 ± 7.1** |
| 4 weeks after last BrdU injection (42 d) Contralateral | 9.95 ± 2.85 | 80 ± 12.3** | 98.4 ± 19.95** | 100.65 ± 19** |

Densitites of newborn cells are presented as the mean number of BrdU-positive cells per $mm^2$ ± SEM. Values different from saline treatment group, $*p < 0.05$, $**p < 0.01$.

TABLE 2

Density of newborn cells in the brain

| Area | Ischemia Only | No Ischemia |
|---|---|---|
| Subventricular zone (BrdU 50 mg/kg ip daily × 14 d) | | |
| 1 day after last BrdU injection (14 d) Right side | 3237.77 × 179.14** | 2301.64 × 171.37 |
| 1 day after last BrdU injection (14 d) Left side | 2361.49 × 156.55 | 2094.06 × 229.20 |
| 4 weeks after last BrdU injection Right side | 272.95 × 32.66 | 222.07 × 21.81 |
| 4 weeks after last BrdU injection Left side | 206.16 × 13.00 | 191.86 × 15.88 |
| Rostral migratory stream (BrdU 50 mg/kg ip daily × 14 d) | | |
| 1 day after last BrdU injection (14 d) Right side | 1185 × 197.65 | 869.2 × 96.25 |
| 1 day after last BrdU injection (14 d) Left side | 1006.75 × 137.1 | 841.9 × 230.4 |
| 4 weeks after last BrdU injection Right side | 38.15 × 20.65 | 21.85 × 6.55 |
| 4 weeks after last BrdU injection Left side | 18.75 × 7.2 | 21.2 × 5.2 |
| Olfactory bulb (BrdU 50 mg/kg ip daily × 14 d) | | |
| 1 day after last BrdU injection (14 d) Right side | 90.7 × 8.6** | 45.15 × 7.4 |
| 1 day after last BrdU injection (14 d) Left side | 48.45 × 5.9 | 31.55 × 8.45 |
| 4 weeks after last BrdU injection (42 d) Right side | 11.4 × 1.45 | 12.95 × 2.6 |
| 4 weeks after last BrdU injection (42 d) Left side | 8.65 × 0.95 | 9.96 × 2.85 |
| Dentate gyrus (BrdU 50 mg/kg ip daily × 14 d) | | |
| 1 day after last BrdU injection (14 d) Right side | 55.11 × 4.06 | 61.31 × 4.49 |
| 1 day after last BrdU Injection (14 d) Left side | 57.00 × 3.99 | 64.44 × 4.13 |
| 4 weeks after last BrdU injection (42 d) Right side | 30.20 × 4.81 | 38.99 × 2.73 |
| 4 weeks after last BrdU injection (42 d) Left side | 29.80 × 4.32 | 40.33 × 3.72 |

Densitites of newborn cells are presented as the mean number of BrdU-positive cells per $mm^2$ ± SEM. Values different from non ischemic group, $*p < 0.05$, $**p < 0.01$.

REFERENCES

Burke and Olson, "Preparation of Clone Libraries in Yeast Artificial-Chromosome Vectors" in Methods in Enzymology, Vol. 194, "Guide to Yeast Genetics and Molecular Biology", eds. C. Guthrie and G. Fink, Academic Press, Inc., Chap. 17, pp. 251–270 (1991).

Capecchi, "Altering the genome by homologous recombination" Science 244:1288–1292 (1989).

Davies et al., "Targeted alterations in yeast artificial chromosomes for inter-species gene transfer", Nucleic Acids Research, Vol. 20, No. 11, pp. 2693–2698 (1992).

Dickinson et al., "High frequency gene targeting using insertional vectors", Human Molecular Genetics, Vol. 2, No. 8, pp. 1299–1302 (1993).

Duff and Lincoln, "Insertion of a pathogenic mutation into a yeast artificial chromosome containing the human APP gene and expression in ES cells", Research Advances in Alzheimer's Disease and Related Disorders, 1995.

Huxley et al., "The human HPRT gene on a yeast artificial chromosome is functional when transferred to mouse cells by cell fusion", Genomics, 9:742–750 (1991).

Jakobovits et al., "Germ-line transmission and expression of a human-derived yeast artificial chromosome", Nature, Vol. 362, pp. 255–261 (1993).

Lamb et al., "Introduction and expression of the 400 kilobase precursor amyloid protein gene in transgenic mice", Nature Genetics, Vol. 5, pp. 22–29 (1993).

Pearson and Choi, *Expression of the human b-amyloid precursor protein gene from a yeast artificial chromosome in transgenic mice*. Proc. Natl. Acad. Sci. USA, 1993. 90:10578–82.

Rothstein, "Targeting, disruption, replacement, and allele rescue: integrative DNA transformation in yeast" in Methods in Enzymology, Vol. 194, "Guide to Yeast Genetics and Molecular Biology", eds. C. Guthrie and G. Fink, Academic Press, Inc., Chap. 19, pp. 281–301 (1991).

Schedl et al., "A yeast artificial chromosome covering the tyrosinase gene confers copy number-dependent expression in transgenic mice", Nature, Vol. 362, pp. 258–261 (1993).

Strauss et al., "Germ line transmission of a yeast artificial chromosome spanning the murine $a_1$ (I) collagen locus", Science, Vol. 259, pp. 1904–1907 (1993).

Gilboa, E, Eglitis, M A, Kantoff, P W, Anderson, W F: Transfer and expression of cloned genes using retroviral vectors. BioTechniques 4(6):504–512, 1986.

Cregg J M, Vedvick T S, Raschke W C: Recent Advances in the Expression of Foreign Genes in *Pichia pastoris*, Bio/Technology 11:905–910, 1993

Culver, 1998. Site-Directed recombination for repair of mutations in the human ADA gene. (Abstract) Antisense DNA & RNA based therapeutics, February, 1998, Coronado, Calif.

Huston et al, 1991 "Protein engineering of single-chain Fv analogs and fusion proteins" in Methods in Enzymology (J J Langone, ed.; Academic Press, New York, N.Y.) 203:46–88.

Johnson and Bird, 1991 "Construction of single-chain Fvb derivatives of monoclonal antibodies and their production in *Escherichia coli* in Methods in Enzymology (J J Langone, ed.; Academic Press, New York, N.Y.) 203: 88–99.

Memaugh and Memaugh, 1995 "An overview of phage-displayed recombinant antibodies" in Molecular Methods In Plant Pathology (R P Singh and U S Singh, eds.; CRC Press Inc., Boca Raton, Fla.) pp. 359–365.

What is claimed is:

1. A method of promoting new neuron growth in a patient comprising the step of:
    administering to a patient in need thereof a therapeutic amount of a nitric oxide donor compound selected from the group consisting of DETANONOate, PAPANONOate, S-nitroso-N-acetylpenicillamine, sodium nitroprusside, sodium nitroglycerine, and L-arginine; and phosphodiesterase inhibitors to a patient in need of neuron growth promotion post stroke.

2. A method of augmenting the production of neurons in a patient by administering to a patient in need thereof an effective amount of a nitric oxide donor selected from the group consisting of DETANONOate, PAPANONOate, S-nitroso-N-acetylpenicillamine, sodium nitroprusside, sodium nitroglycerine, and L-arginine; and phosphodiesterase inhibitors to a site in need of augmentation post stroke.

3. A method of increasing neurological function in a patient via new neuron growth by administering to a patient in need thereof an effective amount of a nitric oxide donor selected from the group consisting of DETANONOate, PAPANONOate, S-nitroso-N-acetylpenicillamine, sodium nitroprusside, sodium nitroglycerine, and L-arginine; and phosphodiesterase inhibitors to a site in need of augmentation post stroke.

* * * * *